(12) United States Patent
Dewey et al.

(10) Patent No.: US 10,080,671 B2
(45) Date of Patent: Sep. 25, 2018

(54) TRIAL AND METHOD FOR USE THEREOF (71) Applicant: Warsaw Orthopedic, Inc., Warsaw, IN (US)

(72) Inventors: Jonathan M. Dewey, Memphis, TN (US); Daniel A. Shimko, Germantown, TN (US)

(73) Assignee: Warsaw Orhtopedic, Inc., Warsaw, IN (US)

( * ) Notice: Subject to any disclaimer, the term of this patent is extended or adjusted under 35 U.S.C. 154(b) by 0 days.

(21) Appl. No.: 15/340,749

(22) Filed: Nov. 1, 2016

(65) Prior Publication Data
US 2018/0116824 A1    May 3, 2018

(51) Int. Cl.
*A61F 2/44*    (2006.01)
*A61F 2/46*    (2006.01)

(52) U.S. Cl.
CPC ............ *A61F 2/4684* (2013.01); *A61F 2/442* (2013.01); *A61F 2/4601* (2013.01); *A61F 2/4611* (2013.01); *A61F 2002/4658* (2013.01)

(58) Field of Classification Search
CPC ........ A61F 2/442; A61F 2/447; A61F 2/4611; A61F 2/4684; A61F 2/441; A61F 2/30742; A61F 2310/00023; A61F 2310/00976; A61F 2310/00011; A61F 2310/00293; A61F 2310/00329; A61F 2310/00353; A61F 2210/0004; A61F 2210/0085; A61F 2220/0025; A61F 2220/0041; A61F 2220/005; A61F 2230/0004; A61F 2230/0013; A61F 2230/0019; A61F 2230/0069; A61F 2250/0009; A61B 17/1604; A61B 17/7065; A61B 17/7097; A61B 17/1671; A61B 2017/0256; A61B 2017/30477; A61B 2017/30578; A61B 2017/30604; A61B 2017/30774; A61B 2017/30785; A61B 2017/30878; A61B 2017/30495; A61B 2017/30556; A61B 2017/30563; A61B 2017/30579; A61B 2017/30583; A61B 2017/30586; A61B 2017/30588; A61B 2017/30883; A61B 2017/30884; A61B 2017/30897; A61B 2017/30899; A61B 2017/3092; A61B 2017/485
USPC ....... 623/17.11–17.16; 606/246–279, 92, 93, 606/94, 95, 96, 99, 100
See application file for complete search history.

(56) References Cited

U.S. PATENT DOCUMENTS

| | | |
|---|---|---|
| 5,944,686 A | 8/1999 | Patterson et al. |
| 6,019,765 A | 2/2000 | Thornhill et al. |
| 6,652,534 B2 | 11/2003 | Zucherman et al. |
| 7,169,182 B2 | 1/2007 | Errico et al. |
| 7,316,689 B2 | 1/2008 | Lieberman |
| 7,776,047 B2 | 8/2010 | Fanger et al. |
| 7,972,340 B2 | 7/2011 | Sand et al. |
| 8,002,837 B2 * | 8/2011 | Stream .................. A61B 17/92 623/17.11 |

(Continued)

*Primary Examiner* — Pedro Philogene (57) ABSTRACT

A trial for insertion into a disc space between adjacent vertebrae in order to facilitate sizing of an interbody spinal implant includes an end portion and a shaft portion. The end portion is dimensioned to approximate the dimensions of an available interbody spinal implant. The trial includes passages extending through at least portions of the end portion and the shaft portion to facilitate access to the disc space during use of the trial.

20 Claims, 6 Drawing Sheets

(56) References Cited

U.S. PATENT DOCUMENTS

| | | |
|---|---|---|
| 8,246,630 B2 | 8/2012 | Manzi et al. |
| 8,366,773 B2 | 2/2013 | Schaller et al. |
| 8,529,576 B2 * | 9/2013 | Krueger ............. A61B 17/8819 606/86 R |
| 8,685,031 B2 * | 4/2014 | Kleiner ................... A61F 2/447 606/92 |
| 8,906,028 B2 | 12/2014 | Kleiner et al. |
| 8,968,323 B2 | 3/2015 | McKay |
| 9,186,193 B2 * | 11/2015 | Kleiner .............. A61B 17/8822 |
| 9,345,586 B2 | 5/2016 | Hunt et al. |
| 9,826,988 B2 * | 11/2017 | Kleiner .............. A61B 17/1659 |
| 2007/0213822 A1 | 9/2007 | Trieu |
| 2009/0105775 A1 | 4/2009 | Mitchell et al. |
| 2010/0198140 A1 | 8/2010 | Lawson |

* cited by examiner

TRIAL AND METHOD FOR USE THEREOF

BACKGROUND OF THE INVENTION

Field of the Invention

The present invention is related to a trial used for sizing an interbody spinal implant for insertion into a disc space between adjacent vertebrae. More particularly, the present invention is related to a trial configured to provide access to the disc space and pass material and equipment therethrough. More specifically, the present invention is related to a trial including passages therethrough to permit passing of implantation materials and instruments through the passages and into the disc space.

Description of the Prior Art

Typically, trials are used to facilitate sizing of interbody spinal implants for insertion into a disc space between adjacent vertebrae. Portions of the trials have dimensions corresponding to the sizes of available interbody spinal implants, and these portions are inserted into the disc space. During surgery, a surgeon can use different sizes of trials to determine which of the sizes of available interbody spinal implants is suitable for implantation. By their very nature, use of the trials entails accessing the disc space. As such, there is a need to maximize use of the access to the disc space afforded by the trials.

SUMMARY OF THE INVENTION

The present invention contemplates a trial used in sizing an interbody spinal implant for insertion into a disc space between adjacent vertebrae, the trial including a leading end, an opposite trailing end, a length extending from the leading end to the trailing end, and a longitudinal axis extending through the leading end and the trailing end, a shaft portion extending from the trailing end toward the leading end, the shaft portion including a first passage therethrough, an end portion positioned at the leading end, the end portion including a leading end surface, a top surface, a bottom surface, a first side surface, a second side surface, and a second passage extending therethrough, the first and second passages communicating with one another, the second passage extending from the first passage to at least a first exit port positioned through one of the leading end surface, the first side surface, and the second side surface, an instrument configured for insertion through at least portions of the first and second passages, the instrument being moveable from a first position to a second position in the first and second passages to facilitate pushing of implantation materials received in the first and second passageways out of the first exit port, where dimensions of the end portion are sized to approximate dimensions of the interbody spinal implant.

The present invention further contemplates a trial used in sizing an interbody spinal implant for insertion into a disc space between adjacent vertebrae, the trial including a shaft portion having a first end, a second end, and a first passage extending between the first and second ends, an end portion extending from the second end of the shaft portion, the end portion including a leading end surface, a top surface, a bottom surface, a first side surface, a second side surface, and a second passage extending therethrough, the first and second passages communicating with one another, the second passage extending from the first passage to at least a first exit port positioned through one of the leading end surface, the first side surface, and the second side surface, where dimensions of the end portion are sized to approximate dimensions of the interbody spinal implant, and where implantation materials received in the first and second passages can be pushed through the first exit port.

The present invention still further contemplates a method of using a trial to size an interbody spinal implant for implantation into a disc space of between adjacent vertebrae of a patient, the method including providing the trial having a shaft portion and an end portion, the shaft portion including a first passage therethrough, the second portion including a second passage therethrough, the first and second passages communicating with one another, and the end portion having a top surface, a bottom surface, a first side surface, a second side surface, and a leading end surface, contacting the top surface of the end portion with an upper of the adjacent vertebrae, and the bottom surface of the bottom portion with a lower of the adjacent vertebrae, positioning the end portion of the trial into the disc space between the adjacent vertebrae, providing an implantation material in the first passage, pushing the implantation material through the first and second passages using an instrument inserted into the trial, and expelling the implantation material from a first exit port formed in at least one of the leading end surface, the first side surface, and second side surface.

These and other objects of the present invention will be apparent from review of the following specification and the accompanying drawings.

DETAILED DESCRIPTION OF THE PREFERRED EMBODIMENT

The trial of the present invention is generally referenced by the numeral 10 in FIGS. 1-8. The trial 10 is used during surgery to facilitate sizing of an interbody spinal implant prior to insertion of the implant into a disc space between adjacent vertebrae V. Furthermore, the trial 10 is configured to afford the passage of implantation materials and/or instruments therethrough.

Figure 10:
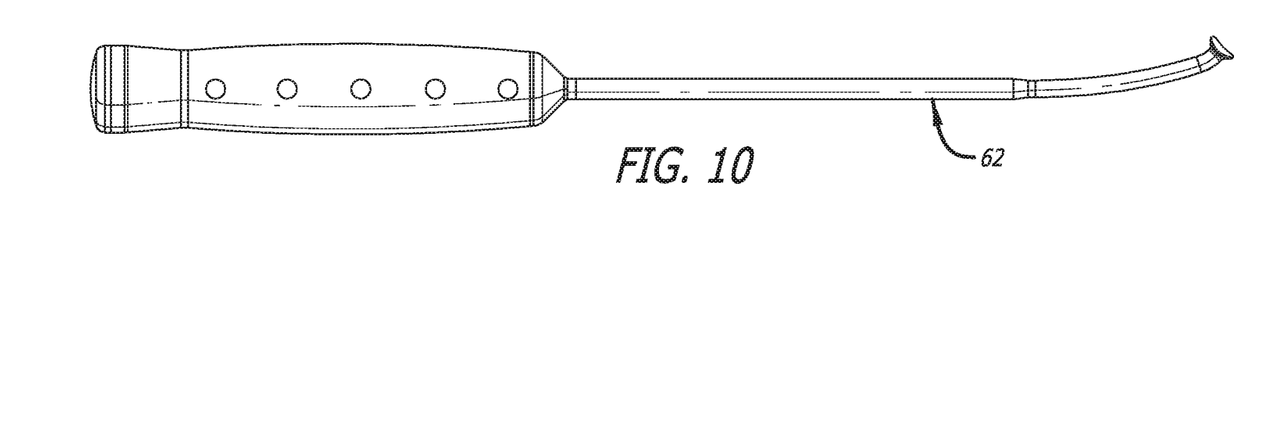
FIG. 10 is a side elevational view of an impactor instrument for insertion through the trials of FIGS. 1 and 7.
Figure 11:
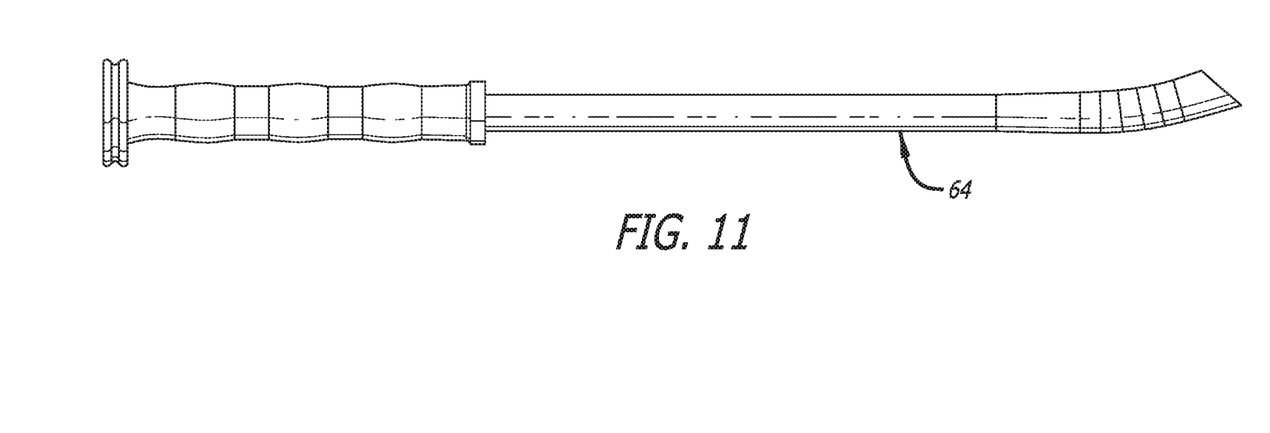
FIG. 11 is a side elevational view of a delivery-tube instrument for insertion through the trials of FIGS. 1 and 7.

Materials passable through the trial 10 include various bone growth promoting substances such as bone morphogenetic protein (BMP), bone graft, crushed bone, bone cement, etc. Instruments passable through the trial 10 include pushers (or tamps) 50 and 60 (depicted in FIGS. 4-6, 8, and 9), an impactor 62 (depicted in FIG. 10), and a delivery tube 64 (depicted in FIG. 11). Portions of the pushers 50 and 60, the impactor 62, and the delivery tube 64 can be flexible to facilitate insertion thereof through the trial 10.

Typically, a variety of trials of different sizes are used during surgery. The end portions of the trials have sizes approximately corresponding to the sizes of interbody spinal implants available for implantation into the disc space. As their name suggests, the differently-sized trials are used as experiments to determine the appropriate size of the interbody spinal implant to be inserted into the disc space. For example, during surgery, a surgeon can iteratively insert trials with progressively larger or smaller end portions into the disc space to determine the appropriate size for the interbody spinal implant.

As depicted in FIGS. 1-6, the trial 10 includes an end portion 11 having a first end 12, and an opposite second end 14, and a length extending between the first and second ends 12 and 14. Furthermore, the end portion 11 is dimensioned to approximate the dimensions of an interbody spinal implant (not shown). The trial 10 also includes a shaft portion 16, and the end portion 11 can be integrally formed with or removably attached to the shaft portion 16. As depicted in FIGS. 1-6, the second end 14 of the end portion 11 is attached to a first end 18 of the shaft portion 16. The shaft portion 16 can be used as a handle to manipulate and position the end portion 11.

The end portion 11 of the trial 10 can also be dimensioned differently than an interbody spinal implant. As such, the trial 10 could have less or more features than an interbody spinal implant. For example, an interbody spinal implant can include surface features such as one way or generic features for resisting movement within the disc space, whereas the trial could have smooth surfaces. Furthermore, as discussed below, while the implant could have a hook tip (similar to the shape shown in FIGS. 7 and 8) the trial could be straight (FIGS. 1-6). One benefit of the trial being straight, but the implant having a hooked shape, would be to prevent the trial from dragging the placed graft material out from the disc space. The trial could also be hook-shaped (FIGS. 7 and 8), while the implant could be straight (similar to the shape shown in FIGS. 1-6) Additional features included on the trial could include hollow or thin portions for assisting the assessment of depth in the disc space using x-rays, and a flatter or a steeper first end 12 to facilitate introduction into the disc space.

The first end 12 and the second end 14 of the end portion 11 includes a first end surface 20 and a second end surface 22. In addition to the first and second ends 12 and 14, as depicted in FIGS. 1-6, the end portion 11 includes a first side surface 24, a second side surface 26, a top surface 28, and a bottom surface 30. As depicted in FIGS. 1-6, the second side surface 26 is longer than the first side surface 24, and thus, the first end surface 20 is angled with respect to the longitudinal axis of the trial 10. The trial 10 can be oriented for posterior insertion to the right or the left of the lateral midline via rotation thereof about its longitudinal axis. As depicted in FIGS. 1-6, the trial 10 is oriented for posterior insertion to the left of the lateral midline, and the angle of the first end surface 20 in this orientation serves in inhibiting over-insertion of the end portion 11. The trial 10 can also be configured for insertion from anterior, direct lateral, anterolateral, and posterolateral insertion into the disc space between adjacent vertebrae V.

The dimensions of the end portion 11 defined by the first and second end surfaces 20 and 22, the first and second side surfaces 24 and 26, the top surface 28, and the bottom surface 30, and, as discussed, the dimensions of the end portion 11 approximate the dimensions of an interbody spinal implant. As such, the end portion 11 can have various sizes corresponding to the dimensions of available interbody spinal implants.

As depicted in FIGS. 3-6, the trial 10 can be cannulated to facilitate passage of instruments and/or implantation materials therethrough. The trial 10, as depicted in FIGS. 3-6, includes a first passage 32 extending through the shaft portion 16, and a second passage 34 (communicating with the first passage 32) extending through the end portion 11.

The second passage 34 includes an entrance 36 and an exit 37. The entrance 36 abuts the first passage 32 facilitating communication of the first and second passages 32 and 34 with one another. The exit 37 can be positioned on various surfaces of the end portion 11 including the first end surface 20, the first side surface 24, and the second side surface 26, and even on the top surface 28 and the bottom surface 30. Furthermore, the second passage 34 can be curved to accommodate placement of the exit 37 on the first and second side surfaces 24 and 26 and the top and bottom surfaces 28 and 30. As depicted in FIGS. 3-6, the exit 37 is positioned on the second side surface 26, and thus, the second passage 34 is curved toward the second side surfaces 26. Thus, implantation materials and instruments inserted through the first passage 32 are directed through the second passage 34 and out of the exit 37. If the exit 37 is provided on the top and bottom surfaces 28 and 30, the implantation materials could be directed towards either of the endplates of the adjacent vertebrae V. Directing the implantation materials towards the endplates would, for example, be desirable if the bone quality was poor and/or there are voids to fill, and a surgeon intended to compact the bone of the vertebral body and/or fill the voids with graft material to provide a more solid surface for the interbody spinal implant to sit on.

Figures 7, 8:
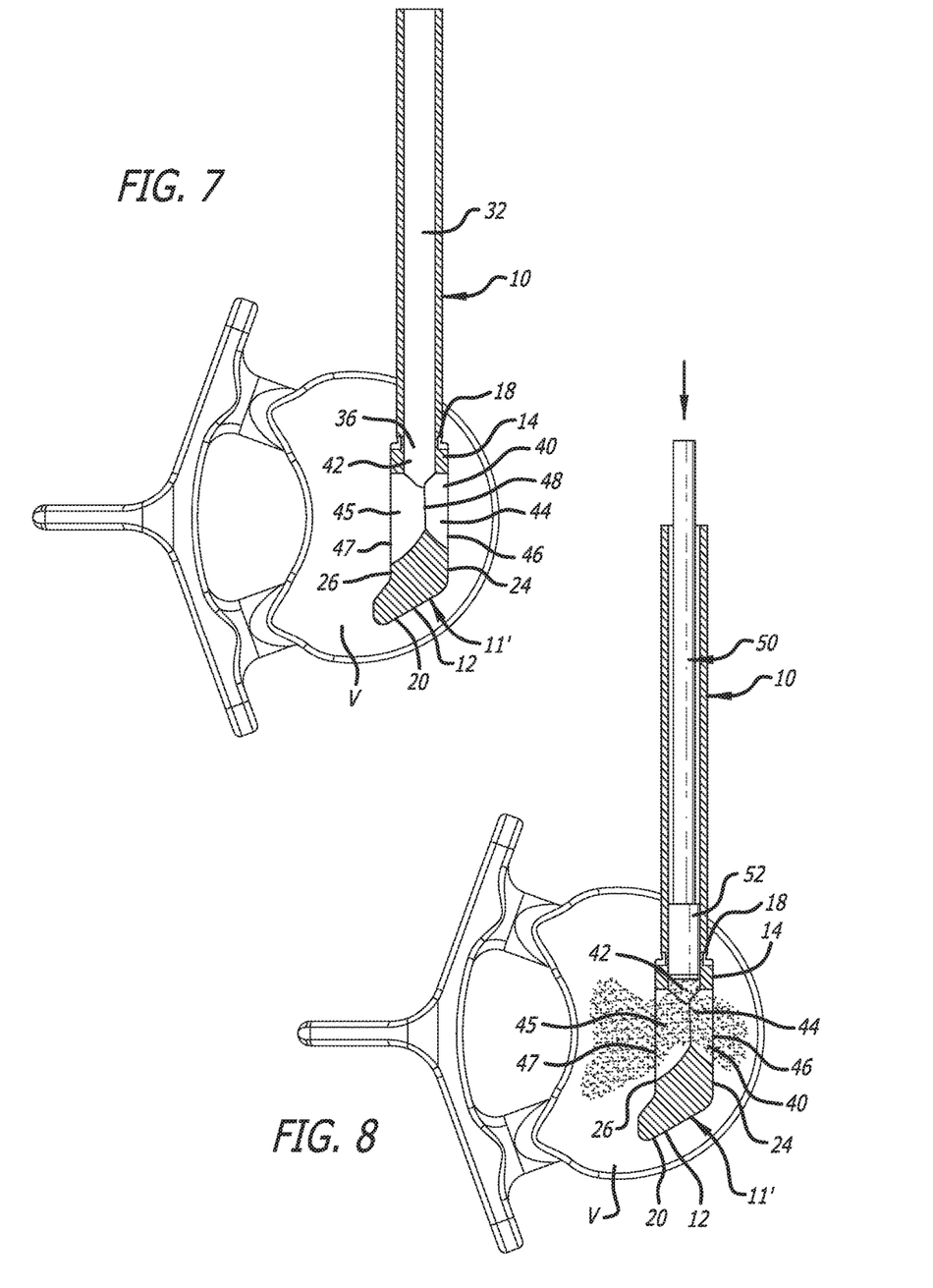
FIG. 7 is a top plan partial cross-sectional view of the trial of FIG. 1 with another embodiment of an end portion showing the trial fully inserted into a disc space from a direct lateral direction, FIG. 7 only depicting a bottom one of the adjacent vertebrae defining the disc space.
FIG. 8 is a top plan partial cross-sectional view of the trial and environment of FIG. 7 showing the trial fully positioned in the disc space, and showing the pusher instrument of FIG. 4 being used to push implantation material through the trial and into the disc space.
Figure 9:
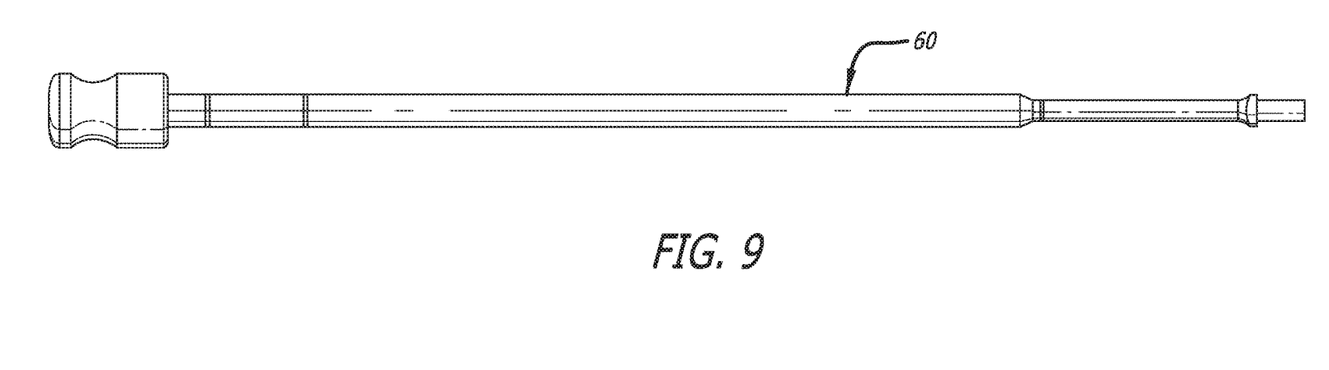
FIG. 9 is a side elevational view of a pusher instrument for insertion through the trials of FIGS. 1 and 7.

Alternatively, the end portion 11 can be modified to have a passage bifurcated with two branches. The modified end portion is generally referred to by the numeral 11' in FIGS. 7 and 8. The end portion 11' includes a passage 40 extending therethrough. The passage 40 can include a stem portion 42, and be bifurcated to include a first branch portion 44 and a second branch portion 45. Exits 46 and 47 of the first and second branch portions 44 and 45, respectively, can be provided on various surfaces of the end portion 11' including the first end surface 20, and the first side surface 24, and the second side surface 26. Furthermore, the first and second branches 44 and 45 can be curved to accommodate placement of the first and second exits 46 and 47 on the first and second side surfaces 24 and 26, respectively. As depicted in FIGS. 7 and 8, the first branch portion 44 extends from the stem portion 42 to the first exit 46 formed on the first side surface 24, and the second branch portion 45 extends from the stem portion 42 to the second exit 47 formed on the second side surface 26.

As depicted in FIGS. 7 and 8, the first and second branches 44 and 45 partially overlap one another, and are separated by a bifurcation area 48. The bifurcation area 48 can be protrusions formed on the interior of the end portion 11' that separate the first and second branches 44 and 45, and define the connection between the stem portion 42 and the first and second branches 44 and 45. The bifurcation area 48, as depicted in FIGS. 7 and 8, is situated such that the first branch 44 is smaller than the second branch 45, and situated such that less of the first branch 44 and more of the second branch 45 communicate with the stem portion 42. Given the location of the bifurcation area 48 and because less of the first branch 44 and more of the second branch 45 communicate with the stem portion 42, more of the material flowing through the passage 40 is shunted to the second branch 45 than the first branch 44.

Alternatively, the first and second branches 44 and 45 can be completely separate from one another, and be formed by completely distinct passages through the end portion 11' such that there is no overlap therebetween. As such, the first and second branches 44 and 45 can have different sizes (e.g., differently-sized cross-sections), and correspondingly have different flow capacities either permitting or restricting flow of implantation materials therethrough. If the first branch 44 has less flow capacity than the second branch 45, the first branch 44 is thus more restrictive to the flow of implantation materials therethrough in comparison to the second branch 45. In other words, if the second branch 45 has more flow capacity than the first branch 44, the second branch 45 is more permissive to the flow of implantation materials therethrough in comparison to the first branch 44. Thus, if the first branch 44 has less and the second branch 45 has more flow capacity in comparison to one another, more of the material flowing through the passage 40 would flow through the second branch 45 than the first branch 44.

During use in spinal surgery, trials 10 having differently-sized end portions 11 can be provided for insertion into the disc space between adjacent vertebrae V. As depicted in FIGS. 1-6, the orientation of the trial 10 affords insertion of the end portion 11 from a posterior approach on the left side of the lateral midline. However, as discussed above, the trial 10 can also be configured for insertion from anterior, direct lateral, anterolateral, and posterolateral insertion into the disc space between adjacent vertebrae V. Depending on the direction of insertion of the trial 10, corresponding incisions in the body of the patient in at least one of an anterior area, a posterior area, and a lateral area can be made. The trials 10 having differently-sized end portions 11 can then be inserted into the body and into the disc space.

Figure 1:
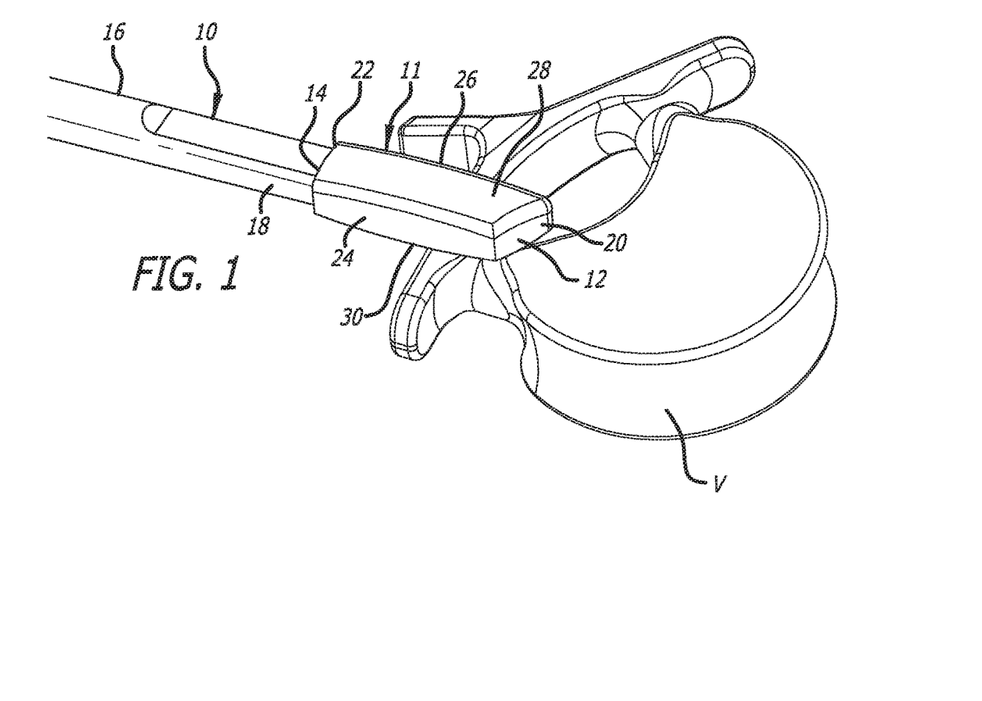
FIG. 1 is a perspective view of a trial being manipulated during surgery to facilitate insertion thereof into a disc space from an posterior direction, FIG. 1 only depicting a bottom one of the adjacent vertebrae defining the disc space.
Figure 2:
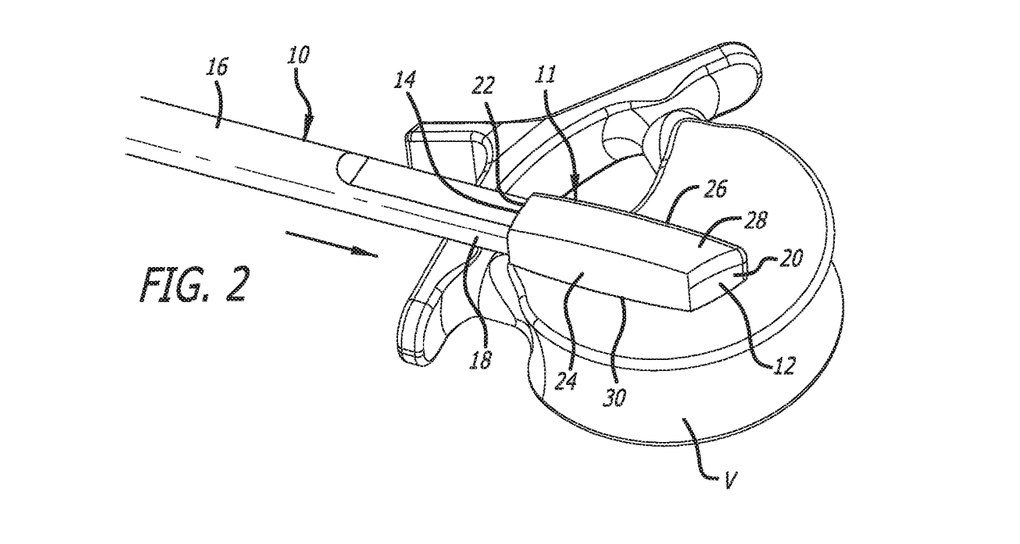
FIG. 2 is a perspective view of the trial and environment of FIG. 1 showing the trial being inserted further into the disc space.
Figure 3:
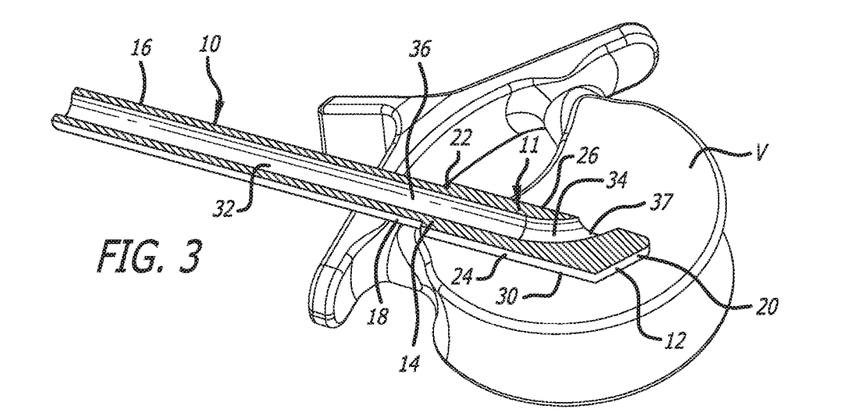
FIG. 3 is a perspective partial cross-sectional view of the trial and environment of FIG. 1 showing the trial fully positioned in the disc space.
Figure 4:
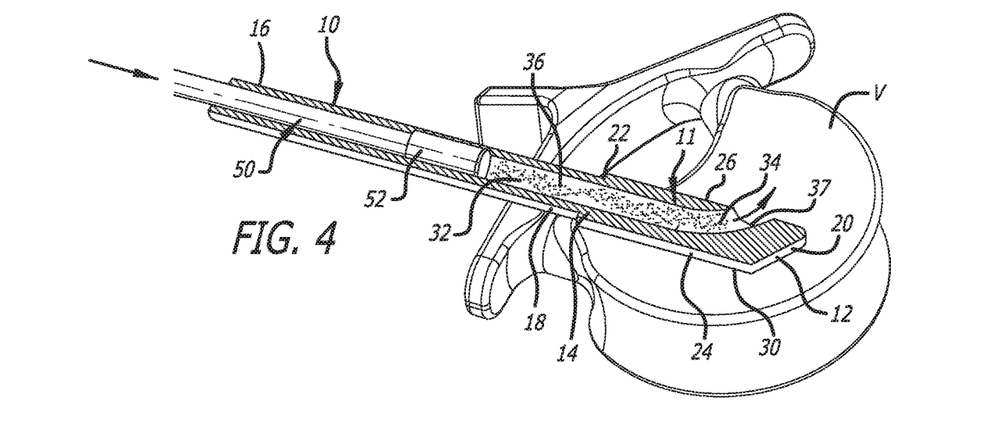
FIG. 4 is a perspective partial cross-sectional view of the trial and environment of FIG. 1 showing the trial fully positioned in the disc space, and showing a pusher instrument in a first position, the pusher instrument being used to push implantation materials through the trial and into the disc space.
Figure 5:
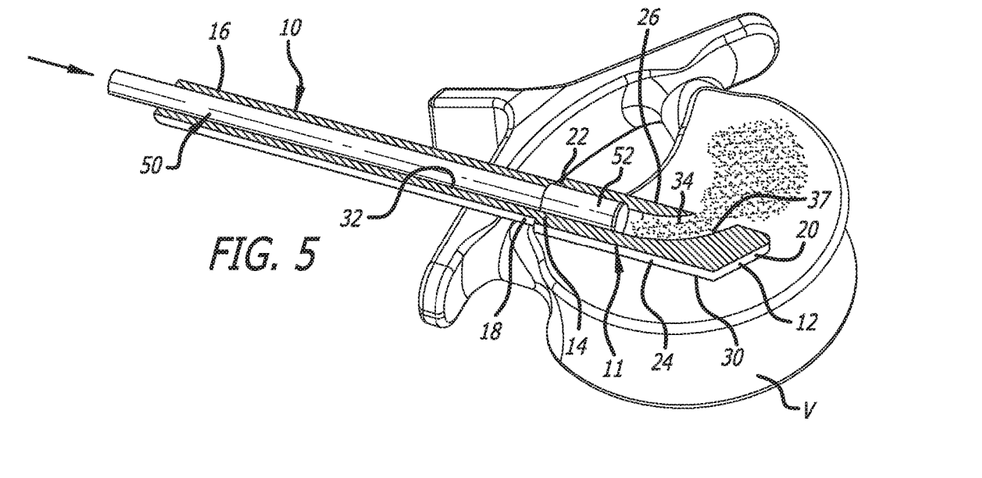
FIG. 5 is a perspective partial cross-sectional view of the trial and environment of FIG. 1 showing the trial fully positioned in the disc space, and showing the pusher instrument of FIG. 4 in a second position, the pusher instrument being used to push implantation material through the trial and into the disc space.
Figure 6:
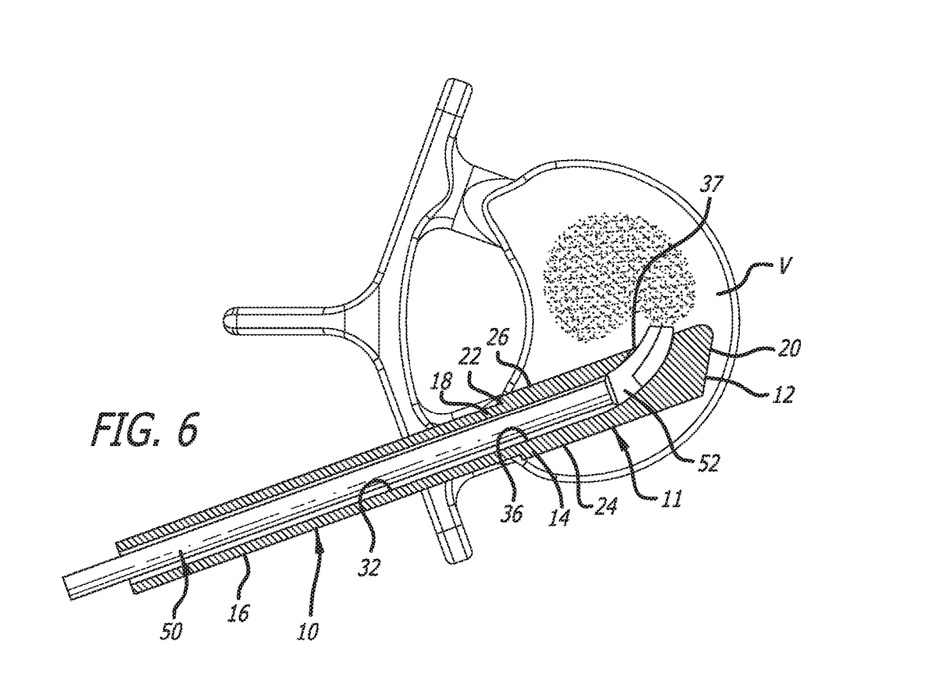
FIG. 6 is a top plan partial cross-sectional view of the trial and environment of FIG. 1 showing the trial fully positioned in the disc space, and showing another embodiment of a pusher instrument being used to push implantation material through the trial and into the disc space.

Once an appropriately-sized end portion 11 is selected, implantation materials and instruments can be inserted through the first and second passages 32 and 34. When implant materials are provided therethrough, as depicted in FIGS. 4-6, the pusher 50 can also inserted through the first and second passage 32 and 34 to push the implantation materials out of exit 37. A head portion 52 of the pusher 50 can be sized according to the size of the second passage 34 to force the implantation materials out of the exit 37. Furthermore, the head portion 52 can be made of flexible materials and/or shaped (FIG. 6) to facilitate insertion thereof through the curvature of second passage 34 when it is curved.

As depicted in FIGS. 3-6, the exit 37 is positioned so that the implantation materials and/or instruments exit the end portion 11 on the second side surface 26 at medial portion of the disc space. However, as discussed above, the exit 37 can be positioned on the first side surface 24 of the end portion 11, so that the implantation materials and/or instruments exit the end portion 11 at a lateral portion of the disc space in FIGS. 3-6. Furthermore, as discussed above, the exit 37 can be positioned on the first end surface 20 of the end portion 11, so that the implantation materials and/or instruments exit the end portion 11 at anterior portion of the disc space.

As depicted in FIGS. 7 and 8, the trial 10 having the end portion 11' is inserted into the disc space from a direct lateral direction. The first and second exits 46 and 47, as depicted in FIGS. 7 and 8 are positioned so the that implantation materials and/or instruments exit the end portion 11' at an anterior portion and a posterior portion, respectively, of the disc space. However, as discussed above, the first and second exits 46 and 47 can also be repositioned on the end portion 11' to afford placement of the implantation materials in different portions of the disc space.

The placement of implantation materials using the trial 10 also creates a space for insertion of the interbody spinal implant. The implantation materials exiting the trial 10 create an area surrounding the end portion 11 or the end portion 11' that define an empty space once the trial 10 is removed from the disc space. The empty space can then be filled by the interbody spinal implant.

Additionally, the trial 10 could also be configured to expand to replicate an expandable interbody spinal implant, and the exits and passages therethrough could be configured within the expansion mechanism to facilitate flow of implantation materials and instruments into specific portions of the disc space.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A trial used in sizing an interbody spinal implant for insertion into a disc space between adjacent vertebrae, the trial comprising:
   a trailing end, an opposite leading end, and a length extending from the trailing end to the leading end, and a mid-longitudinal axis extending through the leading end and the trailing end;
   a shaft portion extending from the trailing end toward the leading end, the shaft portion having a first end collocated with the trailing end, and an opposite second end, the shaft portion including a first passage extending therethrough between the first end and the second end of the shaft portion;
   an end portion extending from the second end of the shaft portion to the leading end, the end portion including a first end adjacent the second end of the shaft portion, an opposite second end, a leading end surface at the second end of the end portion, a top surface, an opposite bottom surface, a first side surface, an opposite second side surface, and a second passage extending therethrough, the first and second passages communicating with one another, the second passage extending from the first passage to a first exit port and a second exit port, the first exit port being positioned on one of the first side surface and the second side surface, and the second exit port being positioned on the other of the first side surface and the second side surface; and an instrument configured for insertion through at least portions of the first and second passages, the instrument being moveable from a first position to a second position in the first and second passages to facilitate pushing of implantation materials received in the first and second passageways out of the first exit port;

wherein dimensions of the end portion are sized to approximate dimensions of the interbody spinal implant; and wherein at least a portion of the first side surface extends in a first plane substantially parallel to the mid-longitudinal axis and at least a portion of the second side surface extends in a second plane substantially parallel to the mid-longitudinal axis, a substantial majority of the end portion being positioned between the first plane and the second plane, and at least a portion of the leading end surface being located on an opposite side of the second plane from the substantial majority of the end portion.

2. The trial of claim 1, wherein the second passage includes a stem portion directly communicating with the first passage in the shaft portion, a first branch portion extending from the stem portion to the first exit port, a second branch portion extending from the stem portion to the second exit port, and a bifurcation area between the first branch and the second branch.

3. The trial of claim 2, wherein the second branch communicates more with the second branch portion than the first branch portion.

4. The trial of claim 1, wherein portions of the first and second branches one of overlap with one another, and are completely separate from one another.

5. The trial of claim 1, wherein the end portion is removably attached to the shaft portion.

6. The trial of claim 5, wherein the end portion includes a trailing end surface opposite from the leading end surface, the trailing end surface provided adjacent an interface of the end portion with the shaft portion.

7. The trial of claim 1, wherein the second passage includes a stem portion directly communicating with the first passage in the shaft portion, a first branch portion extending from the stem portion to the first exit port, a second branch portion extending from the stem portion to the second exit port, and a bifurcation area between the first branch and the second branch.

8. The method of claim 2, wherein at least one of the first branch and the second branch are curved, and the instrument includes a flexible head portion configured for insertion through the one of the first branch and the second branch that is curved.

9. The method of claim 7, wherein at least one of the first branch and the second branch are curved, and the instrument includes a flexible head portion configured for insertion through the one of the first branch and the second branch that is curved.

10. A trial used in sizing an interbody spinal implant for insertion into a disc space between adjacent vertebrae, the trial comprising:

a shaft portion having a first end, an opposite second end, and a first passage extending therethrough between the first and second ends;

an end portion extending from the second end of the shaft portion, the end portion including a first end, an opposite second end, a leading end surface at the second end, a top surface, an opposite bottom surface, a first side surface, an opposite second side surface, and a second passage extending therethrough, the first and second passages communicating with one another, the second passage extending from the first passage to a first exit port and a second exit port, the first exit port being positioned on one of the first side surface and the second side surface, and the second exit port being positioned on the other of the first side surface and the second side surface;

wherein dimensions of the end portion are sized to approximate dimensions of the interbody spinal implant, and wherein implantation materials received in the first and second passages can be pushed through the first exit port; and wherein at least a portion of the first side surface extends in a first plane substantially parallel to the mid-longitudinal axis and at least a portion of the second side surface extends in a second plane substantially parallel to the mid-longitudinal axis, a substantial majority of the end portion being positioned between the first plane and the second plane, and at least a portion of the leading end surface being located on an opposite side of the second plane from the substantial majority of the end portion.

11. The trial of claim 10, further comprising an Instrument configured for insertion through at least portions of the first and second passages, the instrument being moveable from a first position to a second position in the first and second passages to facilitate pushing of implantation materials received in the first and second passageways out of the first exit port.

12. A method of using a trial to size an interbody spinal implant for implantation into a disc space of between adjacent vertebrae of a patient, the method comprising:

providing the trial having a shaft portion and an end portion, the shaft portion including a first end, an opposite second end, and a first passage extending therethrough between the first end and the second end, and the end portion extending from the second end of the shaft portion, the end portion including a first end, an opposite second end, a leading end surface at the second end, a top surface, an opposite bottom surface, a first side surface, an opposite second side surface, and a second passage extending therethrough, the first and second passages communicating with one another, the second passage extending from the first passage to a first exit port and a second exit port, the first exit port being positioned on one of the first side surface and the second side surface, and the second exit port being positioned on the other of the first side surface and the second side surface, at least a portion of the first side surface extending in a first plane substantially parallel to the mid-longitudinal axis and at least a portion of the second side surface extending in a second plane substantially parallel to the mid-longitudinal axis, a substantial majority of the end portion being positioned between the first plane and the second plane, and at least a portion of the leading end surface being located on an opposite side of the second plane from the substantial majority of the end portion;

contacting the top surface of the end portion with an upper of the adjacent vertebrae, and the bottom surface of the bottom portion with a lower of the adjacent vertebrae;

positioning the end portion of the trial into the disc space between the adjacent vertebrae;

providing an implantation material in the first passage;

pushing the implantation material through the first and second passages using an instrument inserted into the trial; and expelling the implantation material from the first exit port and the second exit port.

13. The method of claim 12, further comprising directing the end portion toward the patient using the shaft portion as a handle from one of an anterior, a posterior, a direct lateral, a anterolateral, and a posterolateral direction.

14. The method of claim 12, further comprising inserting the end portion through an incision in the body of the patient in one of an anterior area, a posterior area, and a lateral area.

15. The method of claim 12, further comprising expelling the implantation material from a second exit port formed in at least one of the leading end surface, the first side surface, and the second side surface.

16. The method of claim 15, wherein the second passage includes a first branch communicating with the first exit port, and a second branch communicating with the second exit port, each of the first branch and the second branch includes a curved portion, the pushing of the implantation material further comprising pushing the implantation material through the curved portions of the first and second branches.

17. The method of claim 16, wherein the second passage includes a stem portion communicating directly with the first passage formed in the shaft portion, the stem portion being interposed between the first passage and the first and second branches, the pushing of the implantation material further comprising pushing the implantation material through the stem portion.

18. The method of claim 12, wherein the implantation material is at least one of bone morphogenetic protein (BMP), bone graft, crushed bone, and bone cement.

19. The method of claim 12, wherein the instrument is one of a pusher, an impactor, and a delivery tube.

20. The method of claim 16, wherein the instrument includes a flexible head portion is configured for insertion through the curved portions of the first branch and the second branch.

* * * * *

UNITED STATES PATENT AND TRADEMARK OFFICE
CERTIFICATE OF CORRECTION

PATENT NO. : 10,080,671 B2
APPLICATION NO. : 15/340749
DATED : September 25, 2018
INVENTOR(S) : Dewey et al.

Page 1 of 1

It is certified that error appears in the above-identified patent and that said Letters Patent is hereby corrected as shown below:

On the Title Page

In Item (73), under "Assignee", in Column 1, Line 1, delete "Orhtopedic," and insert -- Orthopedic, --, therefor.

In the Claims

In Column 7, Line 55, in Claim 8, delete "The method of claim 2," and insert -- The trial of claim 2, --, therefor.

In Column 7, Line 60, in Claim 9, delete "The method of claim 7," and insert -- The trial of claim 7, --, therefor.

In Column 8, Line 32, in Claim 11, delete "Instrument" and insert -- instrument --, therefor.

Signed and Sealed this
Sixteenth Day of April, 2019

Andrei Iancu
*Director of the United States Patent and Trademark Office*